US011066634B2

(12) United States Patent
Halverson

(10) Patent No.: US 11,066,634 B2
(45) Date of Patent: Jul. 20, 2021

(54) CULTURE DEVICE AND METHODS FOR ENUMERATING MOLD COLONIES

(71) Applicant: 3M INNOVATIVE PROPERTIES COMPANY, St. Paul, MN (US)

(72) Inventor: Kurt J. Halverson, Lake Elmo, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 199 days.

(21) Appl. No.: 16/196,564

(22) Filed: Nov. 20, 2018

(65) Prior Publication Data

US 2019/0085282 A1 Mar. 21, 2019

Related U.S. Application Data

(62) Division of application No. 14/889,054, filed as application No. PCT/US2014/036730 on May 5, 2014, now abandoned.

(60) Provisional application No. 61/819,690, filed on May 6, 2013.

(51) Int. Cl.
| *C12Q 1/06* | (2006.01) |
| *C12M 1/34* | (2006.01) |
| *C12M 1/12* | (2006.01) |
| *C12M 1/00* | (2006.01) |
| *C12M 1/04* | (2006.01) |
| *C12M 3/00* | (2006.01) |
| *C12Q 1/04* | (2006.01) |

(52) U.S. Cl.
CPC ............ *C12M 41/36* (2013.01); *C12M 23/04* (2013.01); *C12M 23/20* (2013.01); *C12M 23/22* (2013.01); *C12M 23/24* (2013.01); *C12M 23/28* (2013.01); *C12M 23/48* (2013.01); *C12M 25/02* (2013.01); *C12M 25/06* (2013.01); *C12Q 1/045* (2013.01); *C12Q 1/06* (2013.01)

(58) Field of Classification Search
CPC ............ C12N 1/16; C12N 1/18; C12M 41/36; C12M 23/04; C12M 23/20; C12M 23/22; C12M 23/24; C12M 23/28; C12M 23/48; C12M 25/02; C12M 25/06; C12Q 1/045; C12Q 1/06
See application file for complete search history.

(56) References Cited

U.S. PATENT DOCUMENTS

| 4,565,783 A | 1/1986 | Hansen et al. |
| 5,089,413 A | 2/1992 | Nelson et al. |
| 5,601,998 A | 2/1997 | Mach et al. |
| 5,635,367 A | 6/1997 | Lund |

| 2003/0022176 A1 | 1/2003 | Schremp et al. |
| 2004/0152177 A1* | 8/2004 | Anderson, Jr. .......... C12N 1/16 435/142 |
| 2005/0032206 A1 | 2/2005 | Hasegawa |

FOREIGN PATENT DOCUMENTS

| EP | 0 398 703 | 11/1990 |
| EP | 0430151 | * 6/1991 |
| JP | 3-15379 | 1/1991 |
| JP | 2009-153500 | 7/2009 |
| WO | WO 96/06183 | 2/1996 |
| WO | WO 96/38533 | 12/1996 |
| WO | WO 2010/077304 | 7/2010 |
| WO | WO 2010/077619 | 7/2010 |
| WO | WO 2011/090662 | 7/2011 |
| WO | WO 2012/012104 | 1/2012 |

OTHER PUBLICATIONS

US 4,476,226 A, 10/1984, Hansen et al. (withdrawn)
Hardy Diagnostics "Instructions for Use: Malt Extract Agar" 6 pgs , 1996 (Year: 1996).*
Al-Bakri et al. "The assessment of the antibacterial and antifungal activities of aspirin, EDTA and aspirin-EDTA combination and their effectiveness as antibiofilm agents" Journal of Applied Microbiology 107 (2009) 280-286 (Year: 2009).*
Finnegan et al. "EDTA: An Antimicrobial and Antibiofilm Agent for Use in Wound Care" Advances in Wound Care, vol. 4, No. 7, 415-421 (Year: 2015).*
Brazil Search Report for BR112015027917-1 dated Aug. 29, 2019.
Beuchat, L.R. et al.; "Evaluation of Chemicals for Restricting Colony Spreading by a Xerophilic Mold, *Eurotium amstelodami*, on Dichloran—18% Glycerol Agar"; Applied and Environmental Microbiology; vol. 58, No. 6, 1992; pp. 2093-2095.
Brul, S. et al.; "Review—Preservative agents in foods Mode of Action and microbial resistance mechanisms"; International Journal of Food Microbiology; vol. 50; 1999; pp. 1-17.
Choudhary, A.Q. et al.; "Metal-Complexing Agents as Metal Buffers in Media for the Growth of *Aspergillus niger*"; Journal of General Microbiology; vol. 41, No. 41; 1965; pp. 99-107.
Elder, D.P. et al.; "Antimicrobial Preservatives Part Two: Choosing a Preservative"; American Pharmaceutical Review; 2012; 10 pgs.

(Continued)

*Primary Examiner* — Thane Underdahl
(74) *Attorney, Agent, or Firm* — Eric E. Silverman

(57) ABSTRACT

A thin film culture device for enumerating mold colonies is provided. The device comprises water-resistant first and second substrates with a growth region disposed therebetween, a dry, cold water-soluble gelling agent disposed in the growth region, and an effective amount of a calcium-chelating compound disposed in the growth region. The effective amount of calcium-chelating compound is capable of reducing a rate of lateral enlargement of the colony-forming unit growing in the culture device relative to the rate of lateral enlargement of a colony of the same mold species growing in an otherwise identical culture device that does not contain the effective amount disposed in the growth region, wherein reducing the rate of lateral enlargement of the colony-forming unit does not substantially delay detection of the colony. A corresponding method is also provided.

11 Claims, 1 Drawing Sheet

(56) References Cited

OTHER PUBLICATIONS

Henson, O. E.; "Dichloran as an Inhibitor of Mold Spreading in Fungal Plating Media: Effects on Colony Diameter and Enumeration"; Applied and Environmental Microbiology; vol. 42, No. 4, 1981; pp. 656-660.

Hongping, Chen; Food Microorganism Detection Practical Training Course, Zhejiang University Press, Feb. 28, 2011, 26 pgs w-translation.

Jingao, Dong et al.; Research of Plant Physiology and Molecular Biology, May 31, 2009, Science Press, May 31, 2009; 83 pgs w-translation.

Jackson, S.L. et al.; "Roles of Calcium Ions in Hyphal Tip Growth"; Microbiological Reviews; vol. 57, No. 2; 1993; pp. 367-382.

Lew, R.R.; "How does a hypha grow? The biophysics of pressurized growth in fungi"; Nature Reviews/Microbiology; vol. 9; 2011; pp. 509-581.

Qiqin, Shi, et al.; Industry Microorganism Thremmatology, Science Press, Dec. 31, 1991; 11 pgs w-translation.

Sakaguchi, S. et al.; Roles of $Ca^{2+}$ in hyphal and yeast-form growth in *Candida albicans*. Growth regulation by altered extracellular and intracellular free $Ca^{2+}$ concentrations; Mycoscience; vol: 38, Issue 2; 1997; pp. 215-225.

\* cited by examiner

CULTURE DEVICE AND METHODS FOR ENUMERATING MOLD COLONIES

CROSS REFERENCE TO RELATED APPLICATIONS

This is a divisional application of U.S. application Ser. No. 14/889,054, filed Nov. 4, 2015, which is a national stage filing under 35 U.S.C. 371 of PCT/US2014/036730, filed May 5, 2014, which claims priority to U.S. Provisional Application No. 61/819,690, filed May 6, 2013, the disclosures of which are incorporated by reference in their entirety herein.

BACKGROUND

Molds are eukaryotic microorganisms. They are ubiquitous in natural environments, namely, soil, air, water, and plant surfaces. Because of their heterotrophic nature and their ability to adapt to a wide range of environmental conditions, these microbes are frequently encountered as an expensive nuisance in and on various commodities including food ingredients, processed foods, beverages, inadequately cleaned food processing equipment, and food storage facilities. In addition, some yeasts and molds possess potential hazard to human and animal health. For example, numerous molds produce mycotoxins and some mold microorganisms are responsible for human and animal infections.

Mold contamination in food and other commodities can result in substantial economic losses for the producer, the processor, and the consumer. Rapid and accurate determination of mold contamination in a commodity (such as, food ingredients, processed foods, and beverages), is important for the production of high-quality food products in the food industry.

Current practices for routine determination of molds in a food commodity rely largely on conventional culturing techniques for enumerating viable fungal cells on semi-solid agar media. These methods, although widely accepted, have a number of disadvantages in that they are, in general, labor intensive and give low reproducibility. In addition, a common problem encountered in the traditional methods is that the spreading type of mycelial growth of certain molds often over-runs nearby colonies and prevents accurate enumeration of the viable cells in a sample.

SUMMARY

The present disclosure generally relates to the detection and enumeration of mold microorganisms in a sample. In particular, the present disclosure relates to the enumeration of mold colonies in a thin film culture device. The inventors have discovered that thin film culture devices, which lack a head space and have a relatively thinner layer of nutrients (relative to traditional agar Petri dish culture devices), show significant rates of lateral colony expansion (e.g., radial spreading of the colony) for at least some species of mold colonies growing in the devices. The inventors have also discovered that calcium-chelating compounds can be used to reduce the rate of lateral expansion of the growing colonies; surprisingly, without substantially delaying detection of the mold colonies. Advantageously, a reduction in the average colony diameter caused by the calcium-chelating compound permits more accurate enumeration of mold microorganisms in samples that comprise mold species that would otherwise spread over a significant area of the growth region, thereby overlapping other mold colonies and making enumeration of the individual colonies more difficult.

The present disclosure provides a thin film culture device. The culture device can comprise a water-resistant first substrate, a water-resistant second substrate, a growth region disposed between the first and second substrates, a dry, cold water-soluble gelling agent disposed in the growth region, and an effective amount of calcium-chelating compound disposed in the growth region. When the growth region is hydrated with a predetermined volume of aqueous liquid and inoculated with a colony-forming unit of a mold species, the effective amount of calcium-chelating compound is capable of reducing a rate of lateral enlargement of the colony-forming unit growing in the culture device relative to the rate of lateral enlargement of a colony of the same mold species growing in an otherwise identical culture device that does not contain the effective amount disposed in the growth region. Reducing the rate of lateral enlargement of the colony-forming unit does not substantially delay detection of the colony. In any embodiment, the thin film culture device further can comprise a predefined volume of aqueous liquid, wherein the effective amount of the calcium-chelating compound disposed in the growth region is dissolved in the aqueous liquid at a concentration effective to substantially reduce a rate lateral enlargement of a colony of a species of mold growing in the culture device that contains the effective amount disposed in the growth region relative to the rate of lateral enlargement of a colony of the same mold species growing in an otherwise identical culture device that does not contain the effective amount disposed in the growth region.

In another aspect, the present disclosure provides a method for enumerating microorganisms. The method can comprise forming an inoculated culture medium in a growth region of a thin film culture device comprising an effective amount of calcium-chelating compound disposed in the growth region, incubating the inoculated culture medium for a predetermined period of time sufficient to form a macroscopically-detectable colony of a mold microorganism, and counting a number of macroscopically-detectable colonies of mold microorganisms in the growth region. Forming the inoculated culture medium comprises hydrating the growth region with a predetermined volume of aqueous liquid. When the growth region is hydrated with the predetermined volume of aqueous liquid and inoculated with a colony-forming unit of a mold species, the calcium-chelating compound reduces a rate of lateral enlargement of the colony-forming unit growing in the culture device relative to the rate of lateral enlargement of a colony of the same mold species growing in an otherwise identical culture device that does not contain the effective amount disposed in the growth region. Reducing the rate of lateral enlargement of the colony-forming unit does not substantially delay detection of the colony. In any embodiment, the method further can comprise counting a number of macroscopically-detectable yeast colonies in the growth region. In any embodiment, forming an inoculated culture medium can comprise depositing an aqueous sample into the thin film culture device wherein, prior to depositing the aqueous sample, the thin film culture device comprises a nutrient medium, an indicator reagent, and/or the effective amount of the calcium-chelating compound.

In yet another aspect, the present disclosure provides a kit. The kit can comprise a thin film culture device for growing and enumerating mold microorganisms and a container holding a predetermined quantity of a calcium-chelating compound. A portion of the predetermined quantity, when disposed in a growth region of the culture device after the device is inoculated, is sufficient to reduce a rate of lateral enlargement of a colony-forming unit of a mold species growing in the culture device relative to the rate of lateral enlargement of a colony of the same mold species growing in an otherwise identical culture device that does not contain the effective amount disposed in the growth region. Reducing the rate of lateral enlargement of the colony-forming unit does not substantially delay detection of the colony.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a mold microorganism can be interpreted to mean "one or more" mold microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Figure 1:
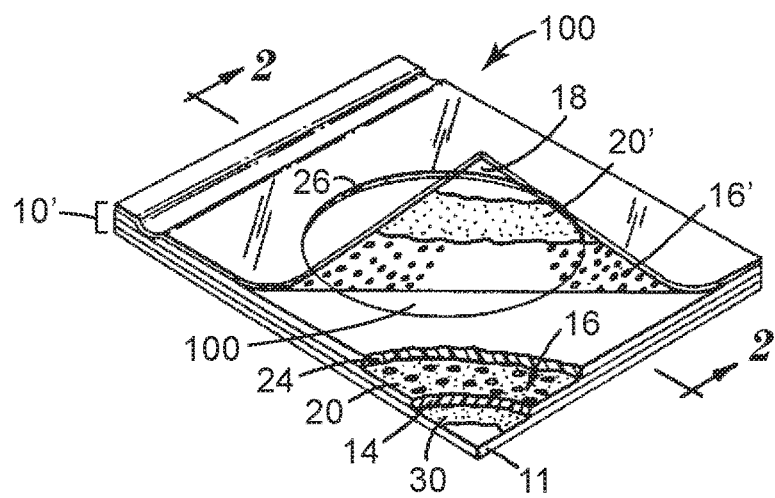
FIG. 1 is a top perspective view of one embodiment of a thin film culture device of the present disclosure.

The present disclosure generally relates to articles and methods for detecting yeast and mold microorganisms. In particular, the present disclosure relates to the detection and enumeration of mold colonies in a thin film culture device.

The structure of thin film culture devices are distinguished from typical culture devices (e.g., petri dishes) for yeast and mold in that thin film culture devices do not have a head space between a surface of the nutrient medium and the surface of the cover for the device. Thus, in contrast to a mold colony growing petri dish, whose cell mass can expand vertically into the head space of the petri dish (thereby, making the colony more visible in the device), the cell mass of a mold colony growing in a thin film culture device must expand horizontally (laterally) through the nutrient medium.

In addition, it is known in the art that the availability of free calcium can affect the growth of mold at the hyphal tips (see, for example, S. L. Jackson and I. B. Heath; Microbiol. Mol. Biol. Re.; 1993; 57:367-382; which is incorporated herein by reference in its entirety). In particular, limiting the amount of free calcium in the region of a mold hyphal tip can significantly reduce the rate of growth at the hyphal tips. The inventive articles and method exploit the effect (e.g., inhibition of elongation of mold hyphae) of a calcium-chelating compound that is commonly used as a preservative to prevent mold growth, by using an amount of chelating agent that is effective to permit growth without substantially delaying detection of the colony. Surprisingly, the amount of chelating agent used is substantially higher than what is typically utilized to prevent mold growth when used as a preservative in certain foods.

Without being bound by theory, the present inventors have discovered that the concentration of free calcium ions in a semi-solid nutrient medium is at least one critical factor that influences the rate of lateral expansion of a mold colony growing in a culture device (e.g., a thin film culture device) comprising the nutrient medium. In addition, they have discovered that including an effective amount of a calcium-chelating compound in the nutrient medium reduces the rate and/or extent of the lateral expansion of mold colonies. The inventive use of the growth-retarding compound, however, surprisingly does not substantially delay the detection of mold colonies, relative to a similar culture device that does not comprise an effective amount of the calcium-chelating compound.

"Air-permeable", as used herein, designates a membrane that, when substantially exposed at its edge(s) to air, is sufficiently permeable to air in the horizontal direction (i.e., parallel to its surfaces) to provide an adequate supply of air to the overlying medium in order to support the growth of aerobic microorganisms in the medium.

"Cold-water-reconstitutable", as used herein, designates material that is suspendible in water, e.g., forms a dispersion, solution or gel in room temperature water.

"Cold-water-soluble", as used herein, designates a cold-water reconstitutable material that forms a solution or gel in room temperature water.

"Growth region", as used herein, designates the region of each component of a device in which microorganisms are intended to be grown.

"Powder", as used herein, designates a particulate material, e.g., of nutrient and/or gelling agent, wherein the particles have an average diameter suitable for use in a device of the present disclosure, e.g., an average diameter of less than about 400 μm.

"Reconstituted medium", as used herein, designates a cold-water-reconstitutable medium that has been rehydrated with water or an aqueous test sample.

"Substantially impermeable to microorganisms and water vapor", as used herein, designates second substrates that (i) prevent undesired contamination of the underlying medium during shipping, storage, and use of the device and (ii) avoid desiccation of the medium, i.e., that maintain a level of hydration in a reconstituted medium suitable to support the growth of microorganisms during the incubation period.

"Substantially water-free", as used herein, designates a water content no greater than about the water content of the ambient environment.

Figure 2:
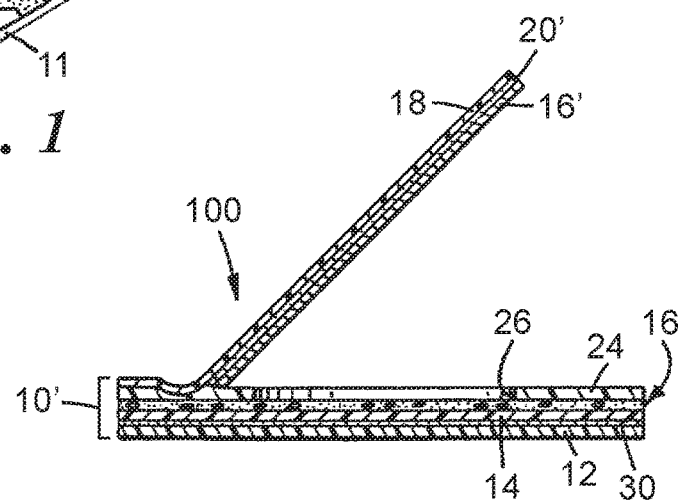
FIG. 2 is a cross-sectional view of the thin film culture device of FIG. 3 taken along line 2-2.

With reference to FIGS. 1 and 2, one embodiment of a thin film culture device 100 of the present disclosure is shown as body member 10 having a water-resistant first substrate 12 and a water-resistant second substrate 18. In any embodiment, preferably, the culture device 100 further comprises an optional air permeable membrane 14. Although these can be arranged in any suitable relationship, FIG. 1 illustrates a preferred arrangement of components, wherein air-permeable membrane 14 is fixed to and is coextensive with at least a growth region 40 of the upper surface of first substrate 12. The culture device 100 includes a first dry coating 16. At least a portion of the first dry coating 16 is disposed in a growth region 40.

In any embodiment of a thin film culture device of the present disclosure, growth region 40 is located between first substrate 12 and second substrate 18 and includes any coating(s), or portion thereof, disposed within the growth region 40 on the first substrate 12 or second substrate 18. The growth region 40 is the location within the culture device that is hydrated with a sample and/or an aqueous suspending medium (e.g., a nutrient broth, sterile water, a buffer) during use of the thin film culture device. In any embodiment, the growth region 40 is located anywhere between the first and second substrates. Preferably, the growth region 40 is spaced apart from the edges of first substrate 12 and second substrate 18 to avoid contamination and/or unacceptable loss of moisture during incubation. In any embodiment, the growth region 40 is defined by a structure (e.g., spacer 24 (see FIGS. 1 and 2), discussed herein) intended to hold a predefined volume of sample and/or aqueous suspending medium.

In any embodiment, the first dry coating 16 comprises a dry, cold water-soluble gelling agent. The first dry coating 16 is typically disposed in the body member 10 on the air-permeable membrane 14, if present, on the first substrate 12 if the air-permeable membrane 14 is not present (not shown) or on the second substrate 18. In any embodiment, the first dry coating 16 further can comprise one or more nutrient to facilitate the growth of a mold microorganism. In any embodiment, the nutrient comprises calcium ions (e.g., a calcium salt). The first dry coating 16 further can comprise an effective amount of calcium-chelating compound, as discussed below. In any embodiment, at least a portion (or the entire amount) of the first dry coating 16 is disposed in the growth region 40 of the thin film culture device.

In any embodiment, a thin film culture device of the present disclosure optionally may comprise a second dry coating (dry coating 16'). Second dry coating 16' may be disposed on the air-permeable membrane 14 (not shown), if present; on the first substrate 12 if the membrane 14 is not present; or on the second substrate 18. In any embodiment, second dry coating 16' can comprise a dry, cold water-soluble gelling agent; a nutrient or mixture of nutrients (optionally, containing a calcium salt), a calcium-chelating compound, a calcium salt, or a combination of any two or more of the foregoing components. In any embodiment, the second dry coating 16' may be identical to the first dry coating 16. In any embodiment, at least a portion (or the entire amount) of the second dry coating 16', if present, is disposed in the growth region 40 of the thin film culture device.

First dry coating 16 and/or second dry coating 16' can be coated onto the first substrate 12 and/or second substrate 18 using the broth coating method of U.S. Pat. No. 4,565,783; the powder coating method of U.S. Pat. No. 5,089,413, or combinations thereof.

Also included in the growth region 40 of the thin film culture device is an effective amount of a calcium-chelating compound. The calcium-chelating compound can be disposed (e.g., as a powder coating) in at least a portion of the growth region 40 in the first dry coating 16 (e.g., as a component of the coating mixture that constitutes the first dry coating 16) and/or the second dry coating 16' (e.g., as a component of the coating mixture that constitutes the second dry coating 16').

Suitable calcium-chelating compounds are soluble in an aqueous liquid. The solubility is sufficiently high to achieve a concentration that reduces the rate of lateral enlargement of a colony of the mold microorganism growing in a thin film culture device (relative to the rate of lateral enlargement of a colony of the same mold microorganism growing in an otherwise identical thin film culture device that does not comprise the calcium-chelating compound) without substantially delaying detection of the colony in the culture device. Examples of suitable calcium-chelating compounds include, but are not limited to, ethylenediamine tetraacetic acid (EDTA), ethyleneglycol tetraacetic acid (EGTA), citrate, and salts (e.g., sodium salts), hydrates, and solvates thereof. In any embodiment, a salt of a calcium-chelating compound is preferred to the free acid form because the salt form is more soluble in water.

Calcium-sensitive dyes can also be used as a calcium-chelating compound according to the present disclosure, provided the dye does not otherwise substantially inhibit the growth of the mold microorganisms. Examples of calcium-sensitive dyes include, but are not limited to, Chlorophosphonazo III (Bis(4-chloro-2-phosphonobenzolazo)chromotropic acid), Arsenazo III (2,2'-(1,8-Dihydroxy-3,6-disulfonaphthylene-2,7-bisazo) bisbenzenearsonic acid, 2,7-Bis(2-arsonophenylazo) chromotropic acid), Antipyrylazo III (3,6-bis(4-antipyrylazo)-4,5-dihydroxy-2,7-naphthalenedisulfonic acid), Carboxyarsenazo III (2-(2-arsonophenylazo)-7-(2-carboxyphenylazo) chromotropic acid), Tropolone (2-Hydroxy-2,4,6-cycloheptatrien-1-one), Alizarin red (1,2-dihydroxyanthraquinone), Carboxyazo III (Benzoic acid,2,2'-[(1,8-dihydroxy-3,6-disulfo-2,7-naphthalenediyl) bis(azo)]bis-(9CI)), Omega chrome black blue, Eriochrome grey 3BL, Oxyacetazo I, Murexide ammonium purpurate, Eriochrome black T, Arsenazo I (2-(1,8-Dihydroxy-3,6-disulfo-2-naphthylazo) benzenearsonic acid trisodium salt, 3-(2-Arsonophenyl)azo-4,5-dihydroxy-2,7-naphthalenedisulfonic acid trisodium salt), Bromopyrogallol red (5',5"-Dibromopyrogallolsulfonephthalein), Bromopyrogallol purple, Methylthymol blue, Calcein, Orthocresolphthalein complexone, and umbelliferone complexone calcein blue (4-methylumbelliferone-8-methylaminodiacetic acid).

The effective amount of calcium-chelating compound may vary depending upon several variables intrinsic and extrinsic variables. One intrinsic variable related to the calcium-chelating compound is the dissociation constant for binding interaction between the calcium-chelating compound and calcium. Another intrinsic variable related to the calcium-chelating compound is the dissociation constant for binding interaction between the calcium-chelating compound and other divalent cations (e.g., Mg) that may be present in the nutrient medium and/or sample and that may interact with the calcium-chelating compound. Two extrinsic variables that can influence the effective amount of calcium-chelating compound are i) the amount of divalent cations (in, particular, calcium ions) present in the nutrient medium and/or sample material used according to the present disclosure and ii) the pH of the nutrient medium and/or sample material. A person having ordinary skill in the art will recognize the dissociation constant of the calcium-chelating compound may be affected by the pH of its surrounding environment. Moreover, a person having ordinary skill in the art also will recognize that the pH effects can be mitigated by the use of a buffer reagent.

Although the range of effective amounts (or concentrations) of calcium-chelating compound discloses herein will be suitable for many situations (food, beverage, or environmental testing), the effective concentration of calcium-chelating compound for a particular sample easily can be determined by making a solution of the compound in an aqueous liquid (e.g., water or Butterfields buffer), making several dilutions (e.g., 2-fold or 5-fold dilutions) of the solution in sterile water or buffer, and following the procedures described in Example 12. The effective amount of any calcium-chelating compound of the present disclosure does not substantially delay detection of a macroscopically-observable colony of a mold microorganism to be detected relative to detection of the mold microorganism in an otherwise identical thin film culture device that does not comprise the calcium-chelating compound.

In any embodiment of a thin film culture device of the present disclosure, the effective amount of calcium-chelating compound is disposed in one or more dry coating (e.g., first dry coating 16 and second dry coating 16') disclosed herein. In any embodiment, the effective amount is disposed in the growth region (e.g., growth region 40) of the culture device. Thus, the proportion of calcium-chelating compound, calcium salt, and the mass of dry coating applied to the growth area are adjusted so that the growth area, when hydrated, comprises a hydrogel having a concentration of calcium-chelating compound that is effective to reduce a rate of lateral enlargement of a colony of the mold microorganisms growing in the culture device without substantially delaying detection of the colony.

In any embodiment, the effective amount of calcium-chelating compound (e.g., disodium ethylenediamine tetraacetic acid dihydrate) is disposed in the thin film culture device in a dry coating having about 0.5 mg to about 12 mg of calcium-chelating compound per 100 $cm^2$. In any embodiment, the effective amount of calcium-chelating compound is disposed in the thin film culture device in a dry coating having about 0.5 mg to about 6 mg of calcium-chelating compound per 100 $cm^2$. In any embodiment, the effective amount of calcium-chelating compound is disposed in the thin film culture device in a dry coating having about 1.0 mg to about 12 mg of calcium-chelating compound per 100 $cm^2$. In any embodiment, the effective amount of calcium-chelating compound is disposed in the thin film culture device in a dry coating having about 1.0 mg to about 6 mg of calcium-chelating compound per 100 $cm^2$. In any embodiment, the effective amount of calcium-chelating compound is disposed in the thin film culture device in a dry coating having about 3.0 mg to about 12 mg of calcium-chelating compound per 100 $cm^2$.

In any method of the present disclosure, discussed in detail below, a portion or the entire effective amount of the calcium-chelating agent can be provided in a dry coating of thin film culture device. Additionally, or alternatively, a portion or the entire effective amount of the effective amount of calcium-chelating compound can be introduced into the culture device in a liquid form before, during, or shortly after inoculation of the culture device with a sample. In any embodiment, the concentration of the calcium-chelating compound in the inoculated culture device can be about 1 mM to about 9.0 mM. In any embodiment, the concentration of the calcium-chelating compound in the inoculated culture device can be about 1 mM to about 5 mM. In any embodiment, the concentration of the calcium-chelating compound in the inoculated culture device can be about 1 mM to about 2 mM.

A person having ordinary skill in the art will recognize that certain samples (e.g., dairy products, sesame seeds, flax seeds) containing relatively high concentrations of calcium may be used in a method of the present disclosure. Optionally, the amount of calcium-chelating compound (either provided in the culture device and/or added to the device when inoculated can be adjusted to offset the higher amount of calcium present in the sample. This approach is shown in Example 5.

The effective amount of calcium-chelating compound reduces the rate of lateral growth of a mold microorganism. Therefore, in any embodiment, after a predefined growth period (i.e., after 48 hours of incubation at 30° C.), the average diameter of a colony of a particular mold species in a thin film culture device comprising the effective amount of calcium-chelating compound is at least about 30% smaller than the average diameter of a colony of the same mold species in a similar thin film culture device without the effective amount of calcium-chelating compound. In any embodiment, after a predefined growth period, the average diameter of a colony of a particular mold species in a thin film culture device comprising the effective amount of calcium-chelating compound is at least about 50% smaller than the average diameter of a colony of the same mold species in a similar thin film culture device without the effective amount of calcium-chelating compound. In any embodiment, after a predefined growth period, the average diameter of a colony of a particular mold species in a thin film culture device comprising the effective amount of calcium-chelating compound is at least about 90% smaller than the average diameter of a colony of the same mold species in a similar thin film culture device without the effective amount of calcium-chelating compound.

Returning to the drawings, first dry coating 16 is fixed to and is coextensive with least the growth region 40 of the top surface of membrane 14, if present, or one of the waterproof substrates (e.g., first substrate 12, as shown in FIGS. 1-4. Second substrate 18; which functions to cover the growth region 40 during shipping, storage, and incubation; is also shown in FIG. 1 as being attached in a hinge-like fashion along one edge of body member 10. Suitable first substrates and second substrates include those described in U.S. Pat. No. 4,565,783, which is incorporated herein by reference in its entirety.

First substrate 12 is preferably a relatively stiff waterproof film made of a material; such as polyester, polypropylene, or polystyrene; that will not absorb or otherwise be adversely affected by water. Polyester films about 100 μm to about 180 μm thick, polypropylene films about 100 μm to about 200 μm thick and polystyrene films about 300 μm to about 380 μm thick are suitable. Other suitable substrates include paper having a polyethylene or other water-proof coating. An example of a suitable polyethylene-coated paper substrate is "Schoeller Type MIL" photoprint paper (available from Schoeller Pulaski, New York). In any embodiment, first substrate 12 can be transparent or translucent if one wishes to view colonies through the first substrate 12.

Air-permeable membrane 14 allows an adequate supply of air to the growth region 40 when second substrate 18 is in place over the growth region 40 during use. In so doing, membrane 14 is useful for supporting growth of aerobic microorganisms (e.g., aerobic filamentous fungi) in the culture devices. It is also useful in instances where the microorganisms require air for reasons in addition to or other than for growth, for example, to oxidize a dye that renders the microorganism colonies more easily visible, as discussed more fully below. Suitable properties and materials for the air-permeable membrane 14 are disclosed in U.S. Pat. No. 5,089,413, which is incorporated herein by reference in its entirety.

In any embodiment, any one of the first substrate 12, second substrate 18 or air-permeable membrane 14 preferably has a visible square grid pattern printed upon it, as shown in U.S. Pat. No. 5,089,413, to facilitate the counting of microorganism colonies.

In any embodiment, first dry coating 16 and/or second dry coating 16' may comprise any suitable form of dry culture medium that is cold-water-reconstitutable and capable of supporting the growth of mold and, optionally, yeast microorganisms. Such media are well known. In any embodiment of the device of the present disclosure, first dry coating 16 contains at least one ingredient selected from the group consisting of one or more gelling agents and one or more nutrients for growing microorganisms (e.g., mold microorganisms.

Suitable gelling agents for use in first dry coating 16 and/or second dry coating 16' include cold-water-soluble natural and synthetic gelling agents. Natural gelling agents such as algin, carboxymethyl cellulose, hydroxyethyl cellulose, guar gum, locust bean gum, xanthan gum, and synthetic gelling agents such as polyacrylamide, are generally suitable. Selection of gelling agent is of particular importance when a device of the invention is intended for use in mold assays. Some gelling agents, such as guar gum, are not suitable for use in certain mold assays because of the ability of molds to metabolize such gelling agents. Appropriate gelling agents can be selected according to the teaching of this invention consistent with the use intended for the device. Preferred gelling agents include locust bean gum and xanthan gum, these gelling agents being useful individually, or preferably, in combination with one another.

As indicated above, first dry coating 16 can contain gelling agent only, and no nutrient. Before the addition of an aqueous sample suspected of containing microorganisms, the user can add nutrients tailored to the type of microorganisms to be grown. For example, dry powdered nutrients can be suspended in a rapidly-evaporating liquid such as ethanol or a volatile chlorofluorocarbon and the suspension can be deposited into the growth area of the device. In other instances, dry powdered nutrients can be suspended, e.g., dispersed or dissolved, in aqueous solutions which can be coated onto (e.g., as described in U.S. Pat. No. 4,565,783) or deposited into the growth area of the culture device. In either case, when an aliquot of the nutrient suspension or solution is added to the surface of the medium, the liquid can be allowed to evaporate, leaving ample nutrients along with the gelling agent. In yet other instances, a nutrient or mixture of nutrients can be added to the aqueous sample before the sample is used to inoculate the culture device, while the sample is inoculated into the culture device and/or after the sample is inoculated into the culture device.

The particular nutrients suitable for use in the thin film culture device may depend on the microorganism to be grown in the device, and will be easily selected by those skilled in the art. Generally, such nutrients are cold-water-soluble.

In any embodiment, first dry coating 16 and/or adhesive layer 20 can include other components, such as dyes, crosslinking agents, or reagents such as antibiotics. For example, for some uses it is desirable to incorporate a dye in the coating, or in the adhesive of an adhered powder medium. Suitable dyes include those that are metabolized by or otherwise react with the growing microorganisms, and in so doing cause the colonies to be colored or fluorescent for easier visualization. Such dyes include chromogenic enzyme substrates such as 5-bromo-4-chloroindolyl phosphate disodium salt, for example. Other suitable dyes include pH-indicating dyes such as neutral red or chlorophenol red, for example.

For some uses it is desirable to have a thin film culture device comprising a dry medium that, when reconstituted, is stiff enough to allow inoculation by streaking. To form a streakable medium, an effective amount of a suitable cross-linking agent can be incorporated into a dry medium that includes a gelling agent. Suitable cross-linking agents do not substantially affect the growth of the intended microorganisms. Suitable types and amounts of cross-linking agents are easily selected by those skilled in the art. For example, with guar gum, cross-linking agents such as potassium tetraborate or aluminum salts are suitable, and can be added in effective amounts, e.g., less than about 1.0 percent by weight of dry medium.

In any embodiment, the thin film culture device can optionally include reagents necessary for carrying out certain microbiological tests. For example, antibiotics can be included for carrying out antibiotic susceptibility tests. For microorganism identification, reagents that undergo a color change in the presence of a particular type of microorganism can be included. To grow a yeast or mold sample without interference from bacteria, bacteriostatic or bacteriocidal agents such as chloramphenicol, chlortetracycline, tartaric acid, or a suitable penicillin can be included in the dry medium.

A thin film culture device of the present disclosure includes second substrate, such as second substrate 18 as illustrated in FIG. 1 for example, adapted to cover at least the growth region 40 of the culture device. In any embodiment, second substrate 18 is preferably transparent in order to facilitate the observation and counting of colonies. In addition, the second substrate 18 is substantially impermeable to microorganisms and water vapor. Generally, second substrate can be made of materials such as those used to make first substrate 12. Since air is supplied to the growth region via air-permeable membrane 14, second substrate need not be selected to allow air transport to the medium. A preferred material for second substrate is polypropylene, e.g., in the form of a 40 µm thick biaxially-oriented polypropylene film.

Second substrate 18 can be free of any coating, or can be coated, e.g., on the surface facing the first substrate 12, in order to facilitate sealing of the second substrate 18 over the growth region 40 of an inoculated thin film culture device. Furthermore, second substrate such as second substrate 18 illustrated in FIGS. 3 and 4, can optionally be coated (e.g., on the surface facing the first substrate 12) with layers of adhesive layer 20' and second dry coating 16'. The adhesive layer 20' may be the same as or different from adhesive layer 20. Second dry coating 16' comprises a cold-water-soluble gelling agent, a nutrient, an indicator reagent, a selective agent, or a combination of any two or more of the foregoing. Coatings on second substrate 18 can cover the entire surface facing the dry coating, but preferably are at least coextensive with the growth region of the medium. Such coated second substrates are particularly preferred when it is desired to provide a device with more gelling agent than can be incorporated in the first dry coating 16 alone.

A device of the invention can also include spacer means between the first dry coating 16 and second substrate 18, in order to create a well that serves to both define the growth region 40 of the first dry coating 16 and to confine an aqueous sample to the growth region 40 of the culture device. One embodiment of a spacer means is illustrated in FIG. 2 as spacer 24 defining a circular hole 26. The walls of hole 26 provide a well having a predetermined size and shape over the growth region 40 of the culture device. Spacer 24 should be thick enough to form a well of the desired volume, e.g., 1, 2, or 3 ml, depending on the size of the growth region and the size of sample to be placed on the medium. In any embodiment, spacer 24 is made of closed cell polyethylene foam. However, any material that is hydrophobic (non-wetting), inert to microorganisms, and, in any embodiment, sterilizable can be used. In any embodiment, the spacer 24 can be coupled (e.g., via a pressure-sensitive adhesive) to the first dry coating 16, the air-permeable membrane 14 (if present), and/or the first substrate 12.

A device of the invention can be prepared using a variety of techniques. Generally, a device can be made by hand or with common laboratory equipment as described, for example, in detail in U.S. Pat. Nos. 4,565,783; 5,089,413; and 5,601,998; which are all incorporated herein by reference in their entirety.

Figure 3:
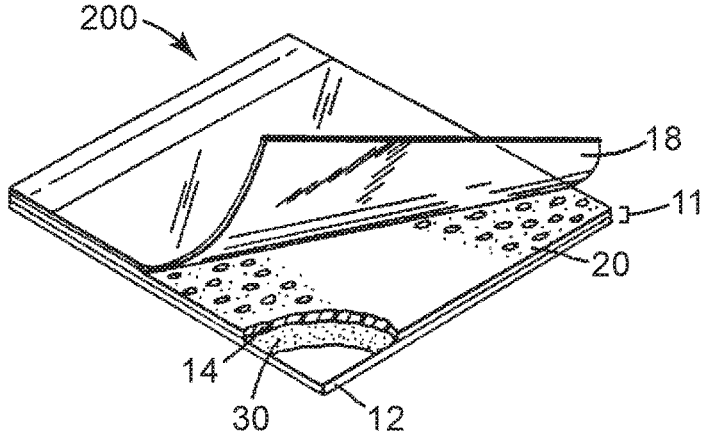
FIG. 3 is a top perspective view, partially in section, of an alternative embodiment of a thin film culture device according to the present disclosure.
Figure 4:
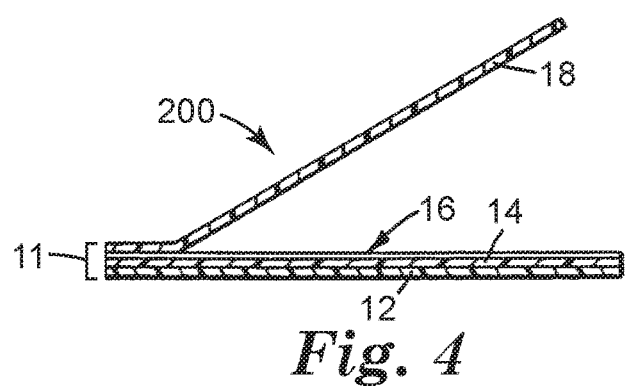
FIG. 4 is a cross-sectional view, partially in section, of the thin film culture device of FIG. 3.

FIGS. 3 and 4 illustrate an alternative embodiment of a device in accordance with the present disclosure. Thin film culture device 200 includes a body member 10' having a water-resistant first substrate 12 with a top surface and a bottom surface. The bottom surface of membrane 14 is fixed to (e.g., fixed with an adhesive or otherwise attached to) at least the growth region 40 of the top surface of substrate 12. In any embodiment, the top surface of first substrate 12 is coated with adhesive layer 30, which is used to fix membrane 14. Adhesive layer 30 is preferably pressure-sensitive, insoluble in water, and substantially non-inhibitory to the growth of the intended microorganisms. Preferred adhesives include those discussed herein in connection with adhesive layers 20 and 20'. Often, suitable substrates are available already coated with a suitable adhesive. If one desires, however, a suitable substrate can be selected and coated (e.g., using a knife coater) with a suitable adhesive.

The method of fixing membrane 14 to first substrate 12 will depend on the nature of adhesive layer 30. If adhesive layer 30 is pressure sensitive for instance, membrane 14 can be placed on adhesive layer 30, pressed down, and thereby adhered in place. First dry coating 16 is fixed in any suitable manner to and covers at least the growth region 40 of membrane 14.

In any embodiment, a first dry coating 16 which may comprise one or more powder, illustrated in FIGS. 3 and 4, is prepared and fixed by first forming a layer of adhesive on at least the growth region of the top surface of membrane 14. The adhesive is preferably pressure-sensitive, insoluble in water, and substantially non-inhibitory to the growth of the intended microorganisms (e.g., mold microorganisms). Preferably, adhesive layer 20 is also sufficiently transparent when wet to enable viewing of microbial colonies.

A nonlimiting example of a suitable pressure-sensitive adhesive is a copolymer of 2-methylbutylacrylate/acrylic acid in a mole ratio of 90/10 (3M Company, St. Paul, Minn.). Other preferred pressure sensitive adhesives that can be used include isooctylacrylate/acrylic acid in a mole ratio of 95/5 or 94/6 (3M Company) and silicone rubber. When incorporating a dye as described above in order to facilitate visualization of colonies, it is generally preferred to incorporate the dye in the adhesive rather than in the powder.

The adhesive is coated (e.g., using a knife coater) onto the top surface of membrane 14 to form a layer with a thickness that is preferably less than the average diameter of the particles of first dry coating 16 or second dry coating 16'. Generally, enough adhesive is coated to adhere the particles to membrane 14 but not so much that the particles become completely embedded in the adhesive. Generally an adhesive layer about 5 µm to about 12 µm thick is suitable.

In order to form an adhered powder medium, a layer of cold-water-soluble powder (first dry coating 16) is then adhered substantially uniformly to at least the growth region of adhesive layer 20.

First dry coating 16 comprises one or more components (e.g., a calcium-chelating compound, a nutrient, an indicator reagent, a selective agent, a gelling agent or a combination of any two or more of the foregoing components) discussed above. Preferably, when the gelling agent is included in first dry coating 16, it is included in an amount such that a predetermined quantity of water or an aqueous sample, e.g., 1 to 3 ml, placed on the medium will form a reconstituted medium having a suitable viscosity, e.g., about 1500 cps or more when measured at 60 rpm with a Brookfield Model L VF viscometer at 25° C. Media of this viscosity allow convenient handling and stacking of the devices during incubation and provide for distinct colony formation in the medium. For instance, 0.025 g to 0.050 g of powdered guar gum spread substantially uniformly over a surface area of 20.3 cm$^2$ will provide a sufficiently viscous medium when reconstituted with 1 to 3 ml of an aqueous sample. The size of the powder particles can be used to control the coating weight per unit area. For example, under conditions where a 100 mesh guar gum coats to a weight of about 0.05 g/20.3 cm$^2$, a 400 mesh guar gum coats to a weight of about 0.025 g/20.3 cm$^2$.

The preferred ratio of gelling agent to nutrient in an adhered powder medium is determined by the particular microorganism to be grown on the device. For general purposes, however, in any embodiment, a ratio from about 4 to 1 to about 5 to 1 (total gelling agent to total nutrient, based on weight) may be preferred. The first dry coating 16, which may consist of powders or agglomerated powders, can be applied to the adhesive layer 20 by any means suitable for the application of a substantially uniform layer. Preferred methods include the use of a shaker-type device, or the use of a powder coater. The other preferred form of dry coating, i.e., a coated medium, is prepared as a substantially water-free coating, coated directly on at least the growth region of the top surface of the membrane, first substrate and/or second substrate. Coated media are generally self-adherent to the membrane and do not require a layer of adhesive between the membrane and the medium.

A coated medium can be prepared by making a solution containing gelling agent and/or nutrient, coating the solution (e.g., using a knife coater) onto the membrane, and allowing the coating of solution to dry. In addition to the suitable gelling agents described above, agar is a suitable cold-water-reconstitutable gelling agent for use in a coated medium. Gelling agent can also serve to thicken the medium solution in order to facilitate its coating onto the membrane. For practical purposes, the amount of gelling agent is preferably less than that which will cause the solution to thicken to the point where it is not practical to coat the medium onto the membrane.

A device of the present invention can also include spacer means. Optional spacer means can be fixed between the first dry coating and a second substrate 18 by any suitable means. For example, it can be adhered to the membrane 14 or first substrate 12 via adhesive layer 20. The spacer can be fixed by pressing it against pressure-sensitive adhesive layer 20.

Second substrate 18 is preferably adhered in a hinge-like fashion along one edge of spacer 24, and is optionally coated with adhesive layer 20' and second dry coating 16'. Alternatively, second substrate 18 can be adhered directly to the substrate 12 (not shown).

A thin film culture device of the present disclosure is particularly useful for growing aerobic microorganisms, and especially aerobic molds. Generally, use of a device of the invention involves the conventional steps of inoculation, incubation and isolation and/or analysis.

In another aspect, the present disclosure provides a method for enumerating mold microorganisms in a sample. The method can be used with any embodiment of the thin film culture devices disclosed herein. The method comprises forming an inoculated culture medium in a thin film culture device, incubating the inoculated culture medium for a predetermined period of time sufficient to form a macroscopically-detectable colony of a mold microorganism, and counting a number of macroscopically-detectable colonies of mold microorganisms in the thin film culture device.

In any embodiment of the method, forming the inoculated culture medium comprises forming a hydrated growth region with a predetermined volume of aqueous liquid. In any embodiment, the sample material (e.g., either a liquid sample, a solid sample, or a solid sample suspended in a liquid) is dissolved or suspended in the predetermined volume and, thus, the sample and the predetermined volume are deposited simultaneously (e.g., by pipetting) into the growth region of the thin film culture device.

Alternatively, in any embodiment, the sample material is deposited into the growth region before the predetermined volume.

Alternatively, in any embodiment, the predetermined volume of liquid is deposited into the growth region and the gelling agent is allowed to swell/hydrate. Subsequently, the culture device is opened and the sample material is deposited onto the hydrated gel. In any embodiment, the sample may be disposed on a sample-capture device such as a membrane filter, for example.

Neither the sample material nor the aqueous liquid used to inoculate the culture device are required to contain nutrients to facilitate the growth of mold microorganisms if the dry coating and/or powder in the culture device comprises nutrients needed for growth of the microorganisms. However, in any embodiment, the sample material and/or aqueous liquid used to inoculate the device may comprise one or more nutrient to facilitate growth of a mold microorganism. In addition, in any embodiment, the sample material and/or aqueous liquid used to inoculate the device may comprise a selective agent (e.g., an antibiotic, an essential nutrient that can be metabolized by certain mold microorganisms and not by other mold microorganisms) that favors growth of all mold microorganisms over other microbes (e.g., bacteria, yeast) that may be present or that favors certain mold microorganisms over other mold microorganisms that may be present.

To use the device of FIGS. 1 and 2, transparent second substrate 18 is pulled back by the user to expose the growth region and a predetermined quantity of aqueous liquid (optionally containing the sample material) is placed, e.g., pipetted, on the first dry coating 16 within the growth region 40 of the culture device. The growth region 40 in the illustrated embodiment is defined by the hole 26 in the spacer 24. The first dry coating 16 thereby becomes reconstituted. Second substrate 18 is then replaced over the reconstituted medium, and the sample is distributed evenly over the growth region, for example by placing a weighted plate on top of the covered device. The device is then incubated at a suitable temperature and for a suitable time in order to allow the growth of microbial colonies. Colonies growing in the medium can be counted by observing them through the second substrate 18. If desired, colonies can be removed from the medium for further identification and/or analysis.

The embodiment of device 11 illustrated in FIGS. 3 and 4 is identical to that of FIGS. 1 and 2 except that spacer 24 is not present in FIG. 3. To use such an embodiment, a template (e.g., a weighted circular ring defining the growth region) can be applied temporarily on top of second substrate 18, after depositing the aqueous liquid onto the growth area and closing the device, to confine reconstitution of the medium to a growth region that is circumscribed by the template. After a period of time during which at least a portion of the gelling agent in the growth region becomes hydrated, the template may be removed from the culture device. Typically, at least a portion of the gelling agent becomes hydrated within 2-3 seconds.

Forming the inoculated culture medium in a thin film culture device, according to the present disclosure comprises forming a hydrated growth region with a predetermined volume of aqueous liquid. When the hydrated growth region is formed, calcium-chelating compound present in the growth area dissolves into the inoculated culture medium at a concentration that is effective to reduce a rate of lateral enlargement of a colony of the mold microorganism growing in the culture device. Surprisingly, the dissolved concentration of the calcium chelating compound reduces the rate of lateral enlargement of a colony of the mold microorganism growing in the culture device without substantially delaying detection of the colony. That is, the colonies typically can be detected after incubating the devices for approximately the same period of time that is customarily used for the same culture medium in a device that lacks an effective amount of a calcium-chelating compound. In any embodiment, the effective amount (i.e., effective concentration, when dissolved in the aqueous liquid) of calcium-chelating compound does not substantially delay detection of a yeast microorganism, if present, that would otherwise be detected within the predetermined period of time.

A person having ordinary skill in the art is well aware of the incubation conditions (e.g., temperature, length of time) that is sufficient to form a macroscopically-detectable colony of a mold microorganism growing in a particular nutrient medium. Typically, the culture device is incubated at a temperature from ambient (approximately 25° C.) to about 32° C. Depending upon the mold microorganism to be detected, the culture device may be incubated for about 40 hours to about 120 hours, inclusive. In any embodiment, the culture device is incubated for about 40 hours to about 96 hours.

Counting a number of macroscopically-detectable colonies of mold microorganisms in the thin film culture device comprises observing colonies that are present in the growth region of the culture device. In any embodiment, observing colonies comprises observing colonies visually. It is contemplated the colonies may be visually observed directly (i.e., an operator observes the culture device) or the colonies may be visually observed indirectly (i.e., an operator observes an image of the culture device). In any embodiment, counting a number of macroscopically-detectable colonies further can comprise counting a second number of macroscopically-detectable colonies of yeast microorganisms.

In any embodiment, the culture device may be imaged using a colony-counting apparatus such as, for example, a PETRIFILM Plate Reader available from 3M Company (St. Paul, Minn.) or a PROTOCOL Colony Counter available from Synbiosis (Cambridge, UK). In any embodiment, mold and/or yeast colonies in the image can be detected and counted using image-analyzing software that is commercially available.

In yet another aspect, the present disclosure provides a kit. The kit can be used in any embodiment of the method of counting mold microorganisms disclosed herein. The kit comprises a thin film culture device for growing and enumerating mold microorganisms and a container holding a predetermined quantity of a calcium-chelating compound. A portion of the predetermined quantity, when disposed in a growth region of the culture device after the device is inoculated, is sufficient to reduce a rate of lateral enlargement of a colony-forming unit of a mold species growing in the culture device relative to the rate of lateral enlargement of a colony of the same mold species growing in an otherwise identical culture device that does not contain the effective amount disposed in the growth region, wherein reducing the rate of lateral enlargement of the colony-forming unit does not substantially delay detection of the colony.

In any embodiment of the kit, the thin film culture device can comprise a water-resistant first substrate, a water-resistant second substrate, a growth region disposed between the first and second substrates, a dry, cold water-soluble gelling agent disposed in the growth region, and an effective amount of a calcium-chelating compound disposed in the growth region. When the growth region is hydrated with a predetermined volume of aqueous liquid and inoculated with a colony-forming unit of a mold species, the effective amount of calcium-chelating compound is capable of reducing a rate of lateral enlargement of the colony-forming unit growing in the culture device relative to the rate of lateral enlargement of a colony of the same mold species growing in an otherwise identical culture device that does not contain the effective amount disposed in the growth region. Reducing the rate of lateral enlargement of the colony-forming unit does not substantially delay detection of the colony.

In any embodiment, the kit further comprises a reagent selected from the group consisting of a nutrient, a detection reagent, a selective agent, a buffering agent, a dye, and a mixture comprising any two or more of the foregoing reagents.

Methods and devices of the present disclosure can be used to reduce the average diameter of mold colonies by about 30%, about 50% or by at least about 90%, relative to an average colony diameter of the mold microorganism grown in a substantially identical thin film culture device that lacks the calcium-chelating compound, after 48 hours of incubation at a temperature suitable for growing the mold microorganism. Surprisingly, even though the lateral expansion of the colonies has been reduced up to 90%, the colonies are still observable within typical incubation times that are used to detect and enumerate mold colonies. Advantageously, the reduction in the average colony diameter permits more accurate enumeration of mold microorganisms in samples that comprise mold species that would otherwise spread over a significant area of the growth region and overlap other mold colonies, making enumeration of the individual colonies more difficult.

Embodiments

Embodiment A is a thin film culture device, comprising:
a water-resistant first substrate;
a water-resistant second substrate;
a growth region disposed between the first and second substrates;
a dry, cold water-soluble gelling agent disposed in the growth region; and
an effective amount of calcium-chelating compound disposed in the growth region;
wherein, when the growth region is hydrated with a predetermined volume of aqueous liquid and inoculated with a colony-forming unit of a mold species, the effective amount of calcium-chelating compound is capable of reducing a rate of lateral enlargement of the colony-forming unit growing in the culture device relative to the rate of lateral enlargement of a colony of the same mold species growing in an otherwise identical culture device that does not contain the effective amount disposed in the growth region;
wherein reducing the rate of lateral enlargement of the colony-forming unit does not substantially delay detection of the colony.

Embodiment B is the thin film culture device of Embodiment A, further comprising a calcium salt disposed in the growth region.

Embodiment C is the thin film culture device of Embodiment A or Embodiment B, wherein the calcium-chelating compound and/or the calcium salt, if present, is disposed in a first dry coating.

Embodiment D is the thin film culture device of any one of the preceding Embodiments, wherein the gelling agent is disposed in the first dry coating and/or in a second dry coating.

Embodiment E is the thin film culture device of any one of the preceding Embodiments, wherein the effective amount of calcium-chelating compound is sufficient to reduce an average colony diameter of a mold microorganism by at least 30%, relative to an average colony diameter of the mold microorganism grown in a substantially identical thin film culture device that lacks the calcium-chelating compound, after 48 hours of incubation at a temperature suitable for growing the mold microorganism.

Embodiment F is the thin film culture device of Embodiment E, wherein the effective amount of calcium-chelating compound is sufficient to reduce an average colony diameter of the mold microorganism by at least 50%, relative to an average colony diameter of the mold microorganism grown in a substantially identical thin film culture device that lacks the calcium-chelating compound, after 48 hours of incubation at a temperature suitable for growing the mold microorganism.

Embodiment G is the thin film culture device of Embodiment F, wherein the effective amount of calcium-chelating compound is sufficient to reduce the average colony diameter of the mold microorganism by at least 90%, relative to an average colony diameter of the mold microorganism grown in a substantially identical thin film culture device that lacks the calcium-chelating compound, after 48 hours of incubation at a temperature suitable for growing the mold microorganism.

Embodiment H is the thin film culture device of any one of the preceding Embodiments, wherein the calcium-chelating compound comprises ethylenediamine tetraacetic acid, ethyleneglycol tetraacetic acid, or citrate.

Embodiment I is the thin film culture device of Embodiment H, wherein the calcium-chelating agent comprises disodium ethylenediamine tetraacetic acid dihydrate, wherein the disodium ethylenediamine tetraacetic acid dihydrate is disposed in a dry coating in the growth region at a coating density of about 0.5 mg to about 12 mg mg/100 cm$^2$.

Embodiment J is the thin film culture device of any one of the preceding Embodiments, further comprising a nutrient medium to support growth of a mold microorganism.

Embodiment K is the thin film culture device of any one of the preceding Embodiments, further comprising an indicator reagent.

Embodiment L is the thin film culture device of any one of the preceding Embodiments, further comprising a predefined volume of aqueous liquid, wherein the effective amount of the calcium-chelating compound disposed in the growth region is dissolved in the aqueous liquid at a concentration effective to reduce a rate lateral enlargement of a colony of a species of mold growing in the culture device that contains the effective amount disposed in the growth region relative to the rate of lateral enlargement of a colony of the same mold species growing in an otherwise identical culture device that does not contain the effective amount disposed in the growth region.

Embodiment M is the thin film culture device of any one of the preceding claims, further comprising an air-permeable membrane adhered to the first substrate, wherein the air-permeable membrane is substantially coextensive with the growth region of the culture device.

Embodiment N is a method for enumerating microorganisms, comprising:

forming an inoculated culture medium in a growth region of a thin film culture device comprising an effective amount of calcium-chelating compound disposed in the growth region;

incubating the inoculated culture medium for a predetermined period of time sufficient to form a macroscopically-detectable colony of a mold microorganism; and counting a number of macroscopically-detectable colonies of mold microorganisms in the thin film culture device;

wherein forming the inoculated culture medium comprises forming a hydrated growth region with a predetermined volume of aqueous liquid;

wherein, when the growth region is hydrated with the predetermined volume of aqueous liquid and inoculated with a colony-forming unit of a mold species, the calcium-chelating compound reduces a rate of lateral enlargement of the colony-forming unit growing in the culture device relative to the rate of lateral enlargement of a colony of the same mold species growing in an otherwise identical culture device that does not contain the effective amount disposed in the growth region;

wherein reducing the rate of lateral enlargement does not substantially delay detection of the colony.

Embodiment O is the method of Embodiment N, wherein the effective amount of calcium-chelating compound does not substantially delay detection of a yeast microorganism, if present, that would otherwise be detected within the predetermined period of time.

Embodiment P is the method of Embodiment O, further comprising counting a number of macroscopically-detectable yeast colonies in the growth region.

Embodiment Q method of any one of Embodiments N through P:

wherein forming an inoculated culture medium comprises depositing an aqueous sample into the thin film culture device;

wherein, prior to depositing the aqueous sample, the thin film culture device comprises a nutrient medium, an indicator reagent, and/or the effective amount of the calcium-chelating compound.

Embodiment R is the method of any one of Embodiments N through Q, wherein incubating the inoculated culture medium for a predetermined period of time comprises incubating the inoculated culture medium between about 40 hours and about 96 hours.

Embodiment S is the method of any one of Embodiments N through R, wherein counting a number of macroscopically-detectable colonies comprises obtaining an image of a growth region of the thin film culture device.

Embodiment T is a kit, comprising:

a thin film culture device for growing and enumerating mold microorganisms; and a container holding a predetermined quantity of a calcium-chelating compound;

wherein a portion of the predetermined quantity, when disposed in a growth region of the culture device after the device is inoculated, is sufficient to reduce a rate of lateral enlargement of a colony-forming unit of a mold species growing in the culture device relative to the rate of lateral enlargement of a colony of the same mold species growing in an otherwise identical culture device that does not contain the effective amount disposed in the growth region;

wherein reducing the rate of lateral enlargement of the colony-forming unit does not substantially delay detection of the colony.

Embodiment U is the kit of Embodiment T, wherein the thin film culture device comprises:

a water-resistant first substrate;

a water-resistant second substrate;

a growth region disposed between the first and second substrates;

a dry, cold water-soluble gelling agent disposed in the growth region; and an effective amount of a calcium-chelating compound disposed in the growth region;

wherein, when the growth region is hydrated with a predetermined volume of aqueous liquid and inoculated with a colony-forming unit of a mold species, the effective amount of calcium-chelating compound is capable of reducing a rate of lateral enlargement of the colony-forming unit growing in the culture device relative to the rate of lateral enlargement of a colony of the same mold species growing in an otherwise identical culture device that does not contain the effective amount disposed in the growth region;

wherein reducing the rate of lateral enlargement of the colony-forming unit does not substantially delay detection of the colony.

Embodiment V is the kit of Embodiment T or Embodiment U, further comprising a reagent selected from the group consisting of a nutrient, a detection compound, a selective agent, a buffering agent, a dye, and a mixture comprising any two or more of the foregoing reagents.

The following EXAMPLES are intended to illustrate the invention. They are not intended to limit the invention.

EXAMPLES

Materials

Unless specified otherwise, all reagents were obtained from Sigma-Aldrich Co.

TABLE 1

List of materials.

| Name | Source |
|---|---|
| Peptic digest of meat, porcine | Alpha Bioscience (Baltimore, MD) |
| Malt extract | EMD (Billerica, MA) |
| Meat Peptone | Becton Dickenson (Franklin Lakes, NJ) |
| Pancreatic digest of Casein | Becton Dickenson (Franklin Lakes, NJ) |
| Proteose peptone | Becton Dickenson (Franklin Lakes, NJ) |
| Disodium EDTA dihydrate | Sigma Aldrich E4884 |
| EGTA | Sigma Aldrich E4378 |
| Yeast extract | Alpha Bioscience |
| Dextrose | Becton Dickenson (Franklin Lakes, NJ) |
| $KH_2PO_4$ | EMD |
| Calcium chloride | Mallinkrodt (Hazelwood, MO) |
| Magnesium sulfate $7H_2O$ | Amresco (Solon, OH) |
| Manganese chloride | Alfa Aesar (Ward Hill, MA) |
| Zinc sulfate $7H_2O$ | EMD |

Examples 1-4. Thin Film Culture Devices for Detecting Mold Microorganisms

Preparation of Nutrient Medium Powder Mixture.

Five batches of non-proteinaceous components 4-11 (Table 2) were weighed into 250 milliliter plastic containers according to the amounts listed in the table. EDTA was added to each batch in the amounts shown in Table 3. After EDTA addition each powder mixture was homogenized in a coffee grinder for 30 seconds (KitchenAid model BCG1110B; KitchenAid; St. Joseph, Mich.). After homogenization, the proteinaceous components 1-3 of Table 1 were added, followed by manual shaking for 30 seconds to mix the powders. Comparative Example 1 was prepared with all of the components except EDTA. "EDTA", as used in the Examples, refers to disodium ethylenediamine tetraacetic acid dihydrate (CAS No. 6381-92-6) obtained from Sigma-Aldrich (St. Louis, Mo.).

TABLE 2

Powder mixtures.

| Component | Name | Mass (g) |
|---|---|---|
| 1 | Peptic digest of meat, porcine | 35 |
| 2 | Malt extract | 22.5 |
| 3 | Yeast extract | 12.5 |
| 4 | Dextrose | 25 |
| 5 | $KH_2PO_4$ | 2.5 |
| 6 | Calcium chloride | 0.5 |
| 7 | Ferric ammonium citrate | 1 |
| 8 | Magnesium sulfate $7H_2O$ | 0.5 |
| 9 | Manganese chloride | 0.5 |
| 10 | Sodium carbonate | 0.5 |
| 11 | Zinc sulfate $7H_2O$ | 0.5 |
| 12 | Disodium EDTA $2H_2O$ | (as shown in Table 2) |

TABLE 3

Amount of disodium EDTA used in each powder formulation.

| | EDTA Mass (g) |
|---|---|
| Comparative Example 1 | 0 |
| Example 1 | 2 |
| Example 2 | 4 |
| Example 3 | 10 |
| Example 4 | 20 |

Preparation of Thin Film Culture Devices.

Dried, powdered gelling agent (300 g) comprising a 1:1 (w/w) mixture of Xanthan/Locust bean gum (XLBG) was added to the blended powders in the amounts shown in table 2 followed by manual shaking for 30 seconds to mix. Culture plates were prepared according to the procedures outlined in U.S. Pat. Nos. 4,476,226 and 5,089,413. Briefly, 3×4 inch (7.6×10.2 cm) sections of bottom film (i.e., the "first substrate" as described herein above) were cut from a master roll. The master roll comprised a hydrophobic-coated paper with a thin layer of adhesive (the noninhibitory adhesive copolymer (approximately 24% solids in a solution in ethyl acetate and heptanes) described in Example 1 of U.S. Pat. No. 5,635,367, which is incorporated herein by reference in its entirety) coated thereon. The adhesive was formulated with Chloramphenicol and Chlortetracycline and was coated onto the master roll essentially as described in Example 1 of U.S. Pat. No. 5,089,413. A foam layer approximately 0.57 mm thick having a 2.4 inch (6.1 cm) diameter circle removed was laminated to each bottom film. Approximately 2 grams of powder was applied to the opening followed by side-to-side and front-to-back movement to evenly distribute the powder on the adhesive. Excess powder was removed by inverting the film, providing a thin layer of the nutrient/gel mixture powder bonded to the adhesive layer. A clear top film comprising an adhesive layer was powder coated with the Xanthan/Locust Bean gum mixture was similarly cut into 7.6×10.2 cm pieces and adhered to the top edge of the bottom film using double sided adhesive tape (3M Company, St. Paul, Minn.). The adhesive layer comprised the adhesive described above mixed with the enzyme substrates shown in Table 4.

TABLE 4

Chromogenic enzyme substrates used to make a thin-film culture device for mold detection.

| Indicator | Indicator Concentration (mg/100 g adhesive) |
|---|---|
| 5-bromo-4-chloro-3-indolyl acetate | 57.7 |
| 5-bromo-4-chloro-3-indolyl-β-D-galactopyranoside | 81.72 |
| 5-bromo-4-chloro-3-indolyl-β-D-glucopyranoside | 81.72 |
| 5-bromo-4-chloro-3-indolyl-α-D-glucopyranoside | 81.72 |
| 5-bromo-4-chloro-3-indolyl phosphate | 86.72 |

Inoculation with *Aspergillus niger* and Incubation of the Thin Film Culture Devices.

Serial dilutions of a frozen stock of *Aspergillus niger* (ATCC 16484) were prepared in Butterfield's Buffer to yield approximately 10 colony forming units (CFU) per milliliter. This film culture devices coated with the powder formulations described above were inoculated by lifting the cover sheet, pipetting 1 milliliter of the diluted sample in the center of the coated bottom film, replacing the cover sheet, and radially distributing the inoculum to the edge of the open circle in the foam laminate by applying downward pressure using the spreading device supplied with 3M PETRIFILM Yeast & Mold Count Plates (hereinafter, "PYM plates"; 3M Company, St. Paul, Minn.). Three replicates were prepared for each powder-coated formulation. After inoculation, the plates were placed in an incubator at 30° C.

Analysis of the Thin Film Culture Devices.

Images of plates were obtained at 42, 48 and 66 hours using a 3M PETRIFILM Plate Reader (3M Company, St. Paul, Minn.) configured to count 3M PETRIFILM Aerobic Count Plates. Colony area was determined using the "count/

Detection of Various Mold Species.

The mold species shown in Table 7 were serially diluted, inoculated, incubated, imaged, and analyzed as described for the *A. niger* cultures. For each mold species the average colony size observed using the thin film culture devices of Examples 1-4 was compared with the average colony size observed using the thin film culture device of Comparative Example 1. The percent reduction in average colony size for the samples is reported in Table 7. For some species a delay in the appearance of visible colonies was observed in culture devices containing EDTA concentrations higher than 1 wt % of the dry powder coatings.

TABLE 7

| Formulation | *Aspergillus niger* 42 hr | *Penicillium variable* 72 hr | *Penicillium chrysogenum* 96 hr | *Cladosporium* sp. 96 hr | *Aspergillus oryzae* 46 hr | *Geotrichum candidum* 46 hr | M97 71 hr |
|---|---|---|---|---|---|---|---|
| Comparative Example 1 | reference | reference | reference | reference | reference | reference | reference |
| Example 1 | −31% | −28% | −35% | −44% | −0%[1] | −0%[2] | −48% |
| Example 2 | −87% | −85% | −61% | −62% | −57% | −44% | −76% |
| Example 3 | −95% | ND[3] | −90% | ND | −85% | −76% | −91% |
| Example 4 | −99% | ND | −98% | ND | −97% | −98% | −99% |

[1]Average colony size of *Aspergillus oryzae* increased by 5% in this concentration of EDTA.
[2]Average colony size of *Geotrichum candidum* increased by 1% in this concentration of EDTA.
[3]Colonies were not detected at this concentration size" function in ImagePro software (Media Cybernetics, Inc.). Histogram-based thresholding was used to establish the edge of the blue colonies using the following intensity values: Red=124-205, Green=182-255 and Blue=112-255. For each image, overlapping (touching) colonies and irregular colonies truncated (i.e., non-circular) by the edge of the inoculated area were excluded from analysis. Mean colony size (calculated using colony diameters from three replicate plates) was determined for each batch of plates after 42 hours of incubation. The results are reported in Table 5.

TABLE 5

Comparison of colony diameters for each formulation.

| Formulation | Number of isolated colonies analyzed | Average colony area (pixels) |
|---|---|---|
| Comparative Example 1 | 14 | 15490 |
| Example 1 | 16 | 10640 |
| Example 2 | 19 | 1950 |
| Example 3 | 4 | 810 |
| Example 4 | 2 | 80 |

Quantitative mold counts were determined after selected periods (42 hours and 66 hours, respectively) of incubation by manually counting the number of blue-colored colonies. The total number of colonies for each set of the replicate culture devices is shown in Table 6.

TABLE 6

| Formulation | 42 hr | 66 hr |
|---|---|---|
| Comparative Example 1 | 22 | 24 |
| Example 1 | 22 | 23 |
| Example 2 | 24 | 26 |
| Example 3 | 4 | 25 |
| Example 4 | 2 | 21 |

Example 5. Detection of Mold in High-Calcium Food Samples Using a Thin Film Culture Device Containing a Calcium-Chelating Compound Fat free skim milk was purchased from a local grocery store. 3.7 milligrams of disodium EDTA dihydrate was added to 10 milliliters of the fat-free skim milk to provide a final concentration of 1 millimolar EDTA. A suspension of *Aspergillus niger* (ATCC #16484) was diluted in Butterfields buffer to a concentration of approximately 500 colony forming units per milliliter. 100 microliters of the diluted suspension was added to the milk sample. After briefly vortexing, 1 milliliter of the milk sample containing the mold was used to inoculate PYM plates according to the manufacturer's instructions. The PYM plates were incubated at 30° C. for 48 hours, followed by imaging and colony size analysis as described above. A control sample (without milk) was also prepared in Butterfield's buffer. Colony size reduction is shown in Table 8.

TABLE 8

| Sample | Colony Area (0 mM EDTA) | Colony Area (1 mM EDTA) | Colony Size Reduction |
|---|---|---|---|
| Skim Milk | 27286 | 3789 | −86% |
| Buffer Control | 37460 | 3276 | −91% |

Example 6. Detection of Yeast Microorganisms Using a Thin Film Culture Device Containing a Calcium-Chelating Compound Thin film culture devices were prepared as described above. Three yeast strains were serially diluted from a frozen stock to provide a final concentration of approximately 100 CFU per ml. The thin film culture devices were inoculated, incubated for 91 hours, imaged, and analyzed as described above. The data showed that colony size for these non-filamentous organisms was not affected by the presence of EDTA at concentrations below 1%. The colony areas were calculated as described for Examples 1-4 and are reported in pixels. *C. glabrata* and *R. mucilaginosa* colonies were not detected in culture devices having EDTA concentrations higher than 1%. The data are shown in FIG. 9.

TABLE 9

Colony area (reported in pixels) for yeast microorganisms.
Each test is reported as the mean ± the standard deviation of the colony area.

| Microorganism | 0% EDTA | 0.5% EDTA | 1% EDTA | 2.3% EDTA | 4.2% EDTA |
|---|---|---|---|---|---|
| C. glabrata | 437 ± 155 | 487 ± 300 | 308 ± 201 | 0 ± 0 | 0 ± 0 |
| R. mucilaginosa | 189 ± 91 | 251 ± 95 | 148 ± 76 | 0 ± 0 | 0 ± 0 |
| C. guillermondi | 553 ± 164 | 490 ± 129 | 201 ± 119 | 381 ± 140 | 162 ± 92 |

Examples 7-11. Thin Film Culture Devices for Detecting Mold Microorganisms

Thin film culture devices were prepared, inoculated, and analyzed as described in Examples 1-4 using the nutrient formulation (lacking the added magnesium sulfate $7H_2O$, manganese chloride, and zinc sulfate $7H_2O$ of the previous Examples) shown in Table 10. EDTA was added as described in Examples 1-4 to attain the final concentrations shown in Table 11. Triplicate plates of each formulation were inoculated with *Aspergillus niger*, incubated, and imaged at 48 and 72 hours, as described for Examples 1-4. The number average colony size after 48 hours of incubation and the number of colonies observed after 48 and 72 hours of incubation is reported in Tables 12 and 13, respectively.

TABLE 10

| Component | Name | Mass (g) |
|---|---|---|
| 1 | Meat peptone | 5.35 |
| 2 | Pancreatic digest of casein | 3 |
| 3 | Yeast extract | 2 |
| 4 | Proteose peptone | 1.25 |
| 5 | Dextrose | 9.1 |
| 6 | $KH_2PO_4$ | 2.5 |
| 7 | Ferric ammonium citrate | 0.21 |
| 9 | Calcium chloride | 0.07 |
| 10 | Sodium carbonate | 0.15 |
| 12 | Disodium EDTA $2H_2O$ | (as shown in Table 9) |

TABLE 11

| | EDTA Mass (g) | EDTA (weight %) |
|---|---|---|
| Comparative Example 2 | 0 | 0 |
| Example 7 | 0.12 | 0.5 |
| Example 8 | 0.18 | 0.75 |
| Example 9 | 0.24 | 1.0 |
| Example 10 | 0.35 | 1.5 |
| Example 11 | 0.47 | 2.0 |

TABLE 12

Colony size after 48 hours of incubation.

| Formulation | Number of isolated colonies analyzed | Average colony size | Reduction in colony size |
|---|---|---|---|
| Comparative Example 2 | 11 | 16662 | Not applicable |
| Example 7 | 11 | 703 | −96% |
| Example 8 | 9 | 107 | −99% |
| Example 9 | 3 | 159 | −99% |
| Example 10 | ND | — | — |
| Example 11 | ND | — | — |

ND—Colonies were not detected by the parameters used for image processing.

TABLE 13

Colony counts after 48 and 72 hours of incubation.

| Formulation | 48 hour colony count | 72 hour colony count |
|---|---|---|
| Comparative Example 2 | 15 | 16 |
| Example 7 | 15 | 17 |
| Example 8 | 11 | 14 |
| Example 9 | 3 | 23 |
| Example 10 | 0 | 14 |
| Example 11 | 0 | 21 |

Example 12. Method of Detecting a Mold Microorganism

In this example EDTA was added to the plates dissolved in the 1 milliliter inoculum instead of being disposed as a component in the coated nutrient formulation, as described above. A diluted suspension of *Aspergillus niger* was prepared as described in example 1. A 1 millimolar solution of EDTA was prepared by dissolving 3.7 milligrams of EDTA in 10 milliliters of Butterfield's buffer. The *Aspergillus niger* diluted suspension was added to the EDTA/Butterfield's to provide a cell concentration of approximately 5 cfu per milliliter. Five replicate devices were prepared by adding one milliliter of the inoculum to PYM plates according to the manufacturer's instructions. A set of control plates was prepared from a 5 cfu per ml solution of *Aspergillus niger* containing no EDTA. Table 14 shows the average colony count per plate after 48 hours and 72 hours of incubation. Table 15 shows that mold colonies growing in 1 mM EDTA had an average colony diameter that was approximately 20-fold smaller than the control plates after 48 hours of incubation.

TABLE 14

| EDTA concentration | CFUs (48 hr) | CFUs (72 hr) |
|---|---|---|
| 0 mM (control) | 15 | 16 |
| 1 mM | 15 | 16 |

TABLE 15

| EDTA concentration | Colony area (pixels) |
|---|---|
| 0 mM (control) | 27840 |
| 1 mM | 1492 |

Example 13. Use of EGTA in a Method of Detecting Mold Microorganisms in a Thin Film Culture Device A 4-millimolar solution of ethylene glycol tetraacetic acid (EGTA) was prepared by dissolving 15.2 milligrams of EGTA in 10 milliliters of Butterfield's buffer. Serial two-fold dilutions were prepared to provide solutions containing 2 millimolar and 1 millimolar EGTA, respectively. "EGTA", as used in the Examples, refers to ethylene glycol-bis(2-aminoethylether)-N,N,N',N'-tetraacetic acid (67-42-5) obtained from Sigma-Aldrich (St. Louis, Mo.). A suspension of *Aspergillus niger* was diluted and added to the solutions as described in Example 12 to provide final cell concentrations of approximately 5 cfu per ml. Three replicate devices were prepared by inoculating 1 milliliter of the mold suspensions to PYM plates according to the manufacturer's instructions. Images of the plates were obtained after 48 hours and 72 hours of incubation, respectively. Quantitative mold counts were determined after selected periods (42 hours and 66 hours, respectively) of incubation by manually counting the number of blue-colored colonies. The total number of colonies for each set of the replicate culture devices is shown in Table 16. Plate counts (total for the three plates) were determined from the image of each plate and the results are shown in Table 16. The average colony size after 48 hours of incubation was determined by imaging the plates and analyzing the images as described above. The results are shown in Table 17.

TABLE 16

| EGTA concentration | 48 hour count | 72 hour count |
| --- | --- | --- |
| 0 mM (control) | 12 | 12 |
| 1 mM | 12 | 12 |
| 2 mM | 14 | 14 |
| 4 mM | 11 | 11 |

TABLE 17

| EGTA concentration | Colony area (pixels) | Reduction in colony area |
| --- | --- | --- |
| 0 mM (control) | 26522 | |
| 1 mM | 24107 | −9% |
| 2 mM | 15177 | −43% |
| 4 mM | 5772 | −78% |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

What is claimed is:

1. A method for enumerating mold microorganisms, comprising:
   contacting an aqueous fluid with a culture medium in a growth region of a thin film culture device to hydrate the growth region,
   exposing aqueous fluid to a dry coating in the growth region;
   incubating the inoculated culture medium for a period of time sufficient to form a macroscopically-detectable colony of a mold microorganism; and
   counting a number of macroscopically-detectable colonies of mold microorganisms in the growth region; wherein
   the growth region comprises
   (a) an effective amount of calcium-chelating compound,
   (b) a nutrient medium capable of supporting the growth of a mild microorganism, and
   (c) the dry coating, the dry coating, wherein the dry coating comprises ethylenediamine tetraacetic acid;
   and wherein, when the step of contacting the growth region with aqueous fluid comprises inoculating the growth region with a colony-forming unit of a mold species, the calcium-chelating compound reduces a rate of lateral enlargement of the colony-forming unit growing in the culture device relative to the rate of lateral enlargement of a colony of the same mold species growing in an otherwise identical culture device that does not contain the effective amount disposed in the growth region;
   without substantially delaying detection of the colony.

2. The method of claim 1:
   wherein forming an inoculated culture medium comprises depositing an aqueous sample into the thin film culture device;
   wherein, prior to depositing the aqueous sample, the thin film culture device comprises a nutrient medium, an indicator reagent, and/or the calcium-chelating compound.

3. The method of claim 1, wherein incubating the inoculated culture medium for a predetermined period of time comprises incubating the inoculated culture medium between about 40 hours and about 96 hours.

4. The method of claim 1, wherein counting a number of macroscopically-detectable colonies comprises obtaining an image of a growth region of the thin film culture device.

5. The method of claim 1, wherein the predetermined volume of aqueous liquid comprises a high calcium food product.

6. The method of claim 1, wherein the predetermined volume of aqueous liquid comprises milk.

7. The method of claim 1, wherein the ethylenediamine tetraacetic acid is sufficient to reduce an average colony diameter of the mold microorganism by at least 50%, relative to an average colony diameter of the mold microorganism grown in a substantially identical thin film culture device that lacks the calcium-chelating compound, after 48 hours of incubation at a temperature suitable for growing the mold microorganism.

8. The method of claim 7, wherein the ethylenediamine tetraacetic acid is sufficient to reduce the average colony diameter of the mold microorganism by at least 90%, relative to an average colony diameter of the mold microorganism grown in a substantially identical thin film culture device that lacks the calcium-chelating compound, after 48 hours of incubation at a temperature suitable for growing the mold microorganism.

9. The method of claim 1, the dry coating comprises a calcium salt.

10. The method of claim 1, wherein the ethylenediamine tetraacetic acid comprises disodium ethylenediamine tetraacetic acid dihydrate.

11. The method of claim 1, the dry coating comprising disodium ethylenediamine tetraacetic acid dihydrate at a coating density of about 0.5 mg/cm$^2$ to about 12 mg/cm$^2$.

* * * * *

UNITED STATES PATENT AND TRADEMARK OFFICE
CERTIFICATE OF CORRECTION

PATENT NO. : 11,066,634 B2
APPLICATION NO. : 16/196564
DATED : July 20, 2021
INVENTOR(S) : Kurt Halverson Page 1 of 1

It is certified that error appears in the above-identified patent and that said Letters Patent is hereby corrected as shown below:

In the Specification

Column 10, Line 34, delete "bacteriocidal" and insert -- bactericidal --

Column 19, Line 13, delete "Mallinkrodt" and insert -- Mallinckrodt --

Column 20, Line 22, delete "noninhibitory" and insert -- non-inhibitory --

Column 23, Line 6, delete "guillermondi" and insert -- guilliermondii --

In the Claims

Column 26, Line 21, delete "the dry coating," after (c)

Column 27, Line 9, delete "claim 1" and insert -- claim 10 --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*